US012736516B2

(12) United States Patent
Rowe et al.

(10) Patent No.: US 12,736,516 B2
(45) Date of Patent: Sep. 15, 2026

(54) PREDICTED BIAS CORRECTION FOR DRILLING FLUIDS

(71) Applicant: Halliburton Energy Services, Inc., Houston, TX (US)

(72) Inventors: Mathew Dennis Rowe, Houston, TX (US); Jhanvi Manishkumar Kevadiya, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 559 days.

(21) Appl. No.: 18/456,117

(22) Filed: Aug. 25, 2023

(65) Prior Publication Data

US 2025/0067716 A1 Feb. 27, 2025

(51) Int. Cl.

| | |
|---|---|
| ***G01N 33/22*** | (2006.01) |
| ***E21B 21/06*** | (2006.01) |
| ***E21B 49/08*** | (2006.01) |
| ***G01N 30/02*** | (2006.01) |
| ***G01N 30/06*** | (2006.01) |
| ***G01N 33/28*** | (2006.01) |
| *G01N 30/88* | (2006.01) |

(52) U.S. Cl.

CPC ......... *G01N 33/225* (2013.01); *E21B 21/067* (2013.01); *E21B 49/086* (2013.01); *G01N 30/06* (2013.01); *G01N 33/2823* (2013.01); *G01N 2030/025* (2013.01); *G01N 2030/062* (2013.01); *G01N 2030/8854* (2013.01)

(58) Field of Classification Search

CPC ... E21B 21/067; E21B 49/086; G01N 33/225; G01N 30/06; G01N 33/2823; G01N 2030/025; G01N 2030/062; G01N 2030/8854

USPC ...................................................... 73/152.23

See application file for complete search history.

(56) References Cited

U.S. PATENT DOCUMENTS

| | | | | |
|---|---|---|---|---|
| 9,458,715 | B2 * | 10/2016 | van Hal | E21B 49/081 |
| 12,000,278 | B2 * | 6/2024 | Chen | E21B 43/12 |
| 2014/0067307 | A1 | 3/2014 | Guerriero et al. | |

(Continued)

OTHER PUBLICATIONS

International Patent Application No. PCT/US2023/072923, International Search Report and Written Opinion mailed May 14, 2024, 9 pages.

*Primary Examiner* — Peter J Macchiarolo
*Assistant Examiner* — Monica S Young
(74) *Attorney, Agent, or Firm* — Kilpatrick Townsend & Stockton LLP

(57) ABSTRACT

A system can displace a headspace associated with a drilling fluid sample with a hydrocarbon blend with a first volume a hydrocarbon gas. The system can also extract the hydrocarbon blend from the head space associated with the drilling fluid sample. The system can further determine a concentration over time of the hydrocarbon gas of the hydrocarbon blend and generating a gas decay curve of the concentration over time of the hydrocarbon gas. Additionally, the system can determine, based on the gas decay curve, a second volume of the at least one hydrocarbon gas. The system may then determine an extraction efficiency correction factor based on a ratio of the first volume to the second volume. The system can correct bias caused by a gas extraction and sampling system during subsequent gas extraction and system operations using the extraction efficiency correction factor.

20 Claims, 6 Drawing Sheets

(56) References Cited

U.S. PATENT DOCUMENTS

| | | | | |
|---|---|---|---|---|
| 2016/0290131 | A1 | 10/2016 | Mitchell et al. | |
| 2017/0268333 | A1 | 9/2017 | Pickell et al. | |
| 2019/0072475 | A1* | 3/2019 | Calleri | E21B 49/086 |
| 2020/0256188 | A1 | 8/2020 | Rowe | |
| 2020/0308963 | A1 | 10/2020 | Dröge | |
| 2023/0273180 | A1* | 8/2023 | Torres-Verdin | G01N 33/2823<br>73/152.18 |

* cited by examiner

PREDICTED BIAS CORRECTION FOR DRILLING FLUIDS

TECHNICAL FIELD

The present disclosure relates generally to wellbore drilling operations and, more particularly (although not necessarily exclusively), to correcting bias in gas extraction and sampling system operations using an extraction efficiency correction factor.

BACKGROUND

During the drilling of subterranean wells, a fluid may circulate through a fluid circulation system that includes a drilling rig and fluid treatment and storage equipment located at or near a surface of a well. The fluid may be pumped by a fluid pump through an interior passage of a drill string, through a drill bit, and back to the surface through an annulus between a wellbore and the drill string. As the well is drilled, fluids, including gases and liquids from the formation, may be released and captured as the fluid is circulated. In some instances, the gases may be wholly or partially extracted from the fluid for analysis, and the fluids may otherwise be analyzed. The gas and fluid analysis may be used to correct wellbore operation data and determine characteristics about the formation. However, for some fluids, such as water-based drilling fluids, a concentration of gas in the fluids may be too low for extraction from samples less than 20 liters. Therefore, current systems for gas and fluid analysis of water-based drilling fluids may require at least a 20-liter drilling fluid sample obtained upon completion of the drilling operation. As a result, gas and fluid analysis by the current systems can be inefficient and correction of drilling operation data may be delayed. Thus, an alternative method allowing for analysis of smaller drilling fluid samples may be desirable. It may further be desirable for the alternative method to involve analyzing the smaller drilling fluid samples before a drilling operation to enable correction of data collected throughout the drilling operation in real-time.

DETAILED DESCRIPTION

Figure 1:
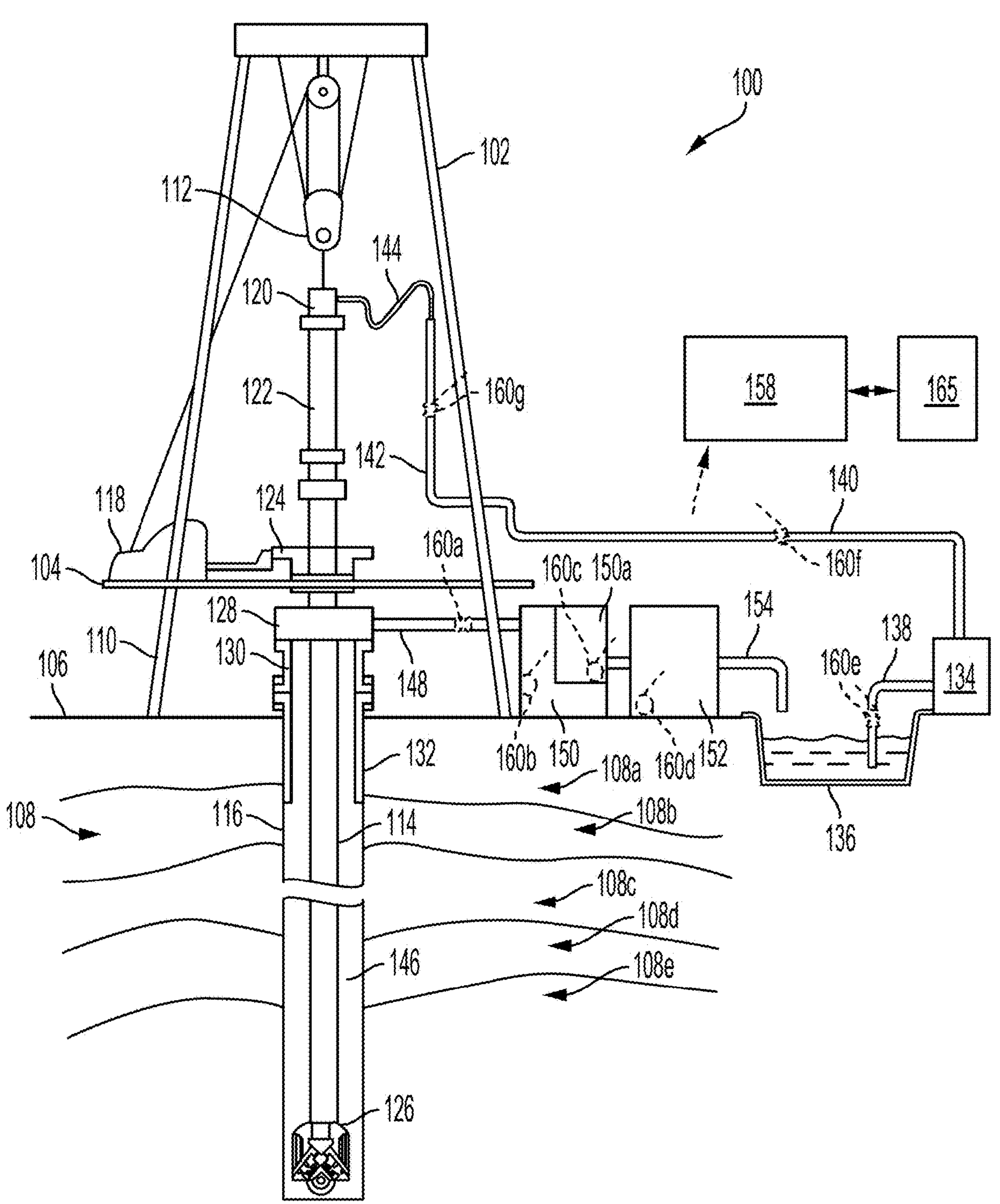
FIG. 1 is an example drilling system, according to one example of the present disclosure.

Certain aspects and examples of the present disclosure relate to predicted bias correction for drilling fluids. Bias can be a measure of how far an analytical result generated with a particular method differs from a theoretical value. Various examples can include performing a gas analysis of drilling fluids prior to a drilling operation. Additionally, various examples of the present disclosure may provide an extraction efficiency correction (EEC) factor for a gas extraction and analysis system while drilling operations are ongoing. Such correction can produce composition results from gas analysis that more accurately represent reservoir compositions for methane through pentane. Bias corrections can be made in real-time at a wellbore site.

In some examples, prior to drilling, a drilling fluid sample can be obtained and positioned in a container, such as a round-bottom flask. The drilling fluid sample can represent a drilling fluid, such as water-based mud (WBM), used during a drilling operation. A headspace of the container, above the drilling fluid sample, can be displaced by a hydrocarbon gas mixture containing one or more hydrocarbon gases with pre-determined volumes. As a result, the one or more hydrocarbon gases (e.g., methane, ethane, propane, isobutane, isopentane, n-pentane) of the hydrogen gas mixture can be in contact with the drilling fluid sample. The drilling fluid sample and the hydrocarbon gas mixture may remain in the container for a period of time (e.g., for two hours) to enable the drilling fluid sample to at least partially absorb the one or more hydrocarbon gases.

After the period of time, the container can be connected to a gas chromatograph or similar equipment to enable analysis of the hydrocarbon gas mixture. Based on the analysis, a concentration per time can be plotted and integrated for each of the hydrocarbon gases. By integrating the concentration per time of each of the hydrocarbon gases, a total volume of each of the hydrocarbon gases in the headspace after the period of time can be determined. The total volume of each of the hydrocarbon gases can be compared to the pre-determined volumes of the hydrocarbon gases. An EEC factor can then be determined based on the comparison of generated values (i.e., the total volumes) and theoretical values (i.e., the pre-determined volumes). Additionally, an amount of each of the hydrocarbon gases absorbed by the drilling fluid sample can be determined based on the comparison. The EEC factor can be used to correct a bias in data obtained during a wellbore operation. The bias may be caused by the drilling fluid at least partially absorbing hydrocarbons during the wellbore operation.

In a particular example, gas inlet and outlet connections of a round bottom flask can be prepared. After the preparation of the round-bottom flask, a known volume (e.g., two hundred and fifty milliliters) of WBM can be positioned in the round bottom flask and may be stirred using a magnetic stirrer. The WBM may also be heat up to a pre-determined temperature while being stirred. A gas inlet of the round-bottom flask may then be connected to a first end of a tube and a second end of the tube can be connected to a calibration gas bottle. Additionally, a gas outlet of the round-bottom flask can be connected to a first end of a vent tube and a second end of the vent tube can be connected to a Gas Chromatograph (GC). A hydrocarbon mixture can then be flushed from the calibration gas bottle into the round-bottom flask to displace a headspace above the WBM in the round-bottom flask. The hydrocarbon mixture can further be measured by the GC. The hydrocarbon mixture may be flushed into the round-bottom flask until the GC is calibrated such that concentrations of hydrocarbon gases in the hydrocarbon mixture measured by the GC are equal or similar to concentrations associated with calibration gas bottle. In an example, the hydrocarbon mixture may be flushed until the concentrations are within five percent of the concentrations associated with the calibration gas bottle.

After calibrating the GC, the gas inlet and gas outlet of the round-bottom flask can be disconnected. The hydrocarbon mixture and WBM can be left in the round-bottom flask for two or more hours. The gas outlet of the round-bottom flask may then be reconnected to the GC. A sample pump with a known flow rate can pump the hydrogen mixture from the headspace of the round-bottom flask into the GC for analysis. In an example, the sample pump can be on until a detected concentration of method is below 50 parts per mission (ppm), then the sample pump can be turned off. Additionally, in some examples, the drilling fluid sample may be heat to a predetermine temperature (e.g., 50 degrees Celsius). Then, once the drilling fluid reaches the predetermine temperature, the pump may be turned on and the drilling fluid may be stirred. This may continue until the drilling fluid sample reaches a second predetermine temperature (e.g., 70 degrees Celsius), then the pump may be turned off. The hydrocarbon mixture provided to the GC via the pump can be analyzed. The analysis of the hydrocarbon mixture by the GC can be performed until a concentration of the hydrogen mixture from the round-bottom flask is below a GC limit of quantification (LOQ). That is, until the amount of hydrocarbon mixture in the round-bottom flask may not be detectable by the GC.

A gas decay curve can be generated based on concentrations over time for each hydrocarbon gas in the hydrocarbon gas mixture measured by the GC. The concentrations over time can then be integrated taking into account the known flow rate of the pump to determine a volume of each hydrocarbon gas in the headspace after the two or more hours. The volume of each hydrocarbon gas can then be compared to theoretical volumes as provided by the calibration gas bottle or measured by the GC during calibration. The comparison can be used to correct biases in data obtained during wellbore operations that involve the WBM. The biases may be caused by the WBM at least partially absorbing the hydrocarbon mixture.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is an example drilling system, according to one example of the present disclosure. The drilling system 100 may include a derrick 102 mounted on a floor 104 that is in contact with a surface 106 of a formation 108 through supports 110. The formation 108 may include a plurality of rock strata 108*a-e*, each of which may be made of different rock types with different characteristics. At least some of the strata may be porous and contain trapped fluids including liquid and gaseous components. Although the drilling system 100 includes an "on-shore" drilling system in which a floor 104 is at or near the surface 106, similar "off-shore" drilling systems are also possible and may be characterized by the floor 104 being separated from the surface 106 by a volume of water.

The derrick 102 may include a traveling block 112 for raising or lowering a drill string 114 disposed within a wellbore 116 in the formation 108. A motor 118 may control the position of the traveling block 112 and, therefore, the drill string 114. A swivel 120 may be coupled between the traveling block 112 and a kelly 122, which supports the drill string 114 as it is lowered through a rotary table 124. A drill bit 126 may be coupled to the drill string 114 and driven by a downhole motor (not shown) or rotation of the drill string 114 by the rotary table 124. As the drill bit 126 rotates, it creates the wellbore 116, which passes through one or more rock strata or layers of the formation 108.

The drill string 114 may extend into the wellbore 116 through a bell nipple 128, blowout preventer (BOP) 130, and wellhead 132. The wellhead 132 may include a portion that extends into the wellbore 116. In certain examples of the present disclosure, the wellhead 132 may be secured within the wellbore 116 using cement. The BOP 130 may be coupled to the wellhead 132 and the bell nipple 128, and the BOP 130 may work with the bell nipple 128 to prevent excess pressures from the formation 108 and wellbore 116 from being released at the surface 106. For example, the BOP 130 may include a ram-type BOP that closes an annulus 146 between the drill string 114 and the wellbore 116 in case of a blowout.

During drilling operations, drilling fluid, such as drilling mud, may be pumped into and received from the wellbore 116. In certain examples of the present disclosure, this drilling fluid may be pumped and received by a fluid circulation system that includes components on and below the surface 106. The fluid circulation system can include fluid containment components, flow actuator components, fluid treatment components and fluid flow conduits through which drilling fluid flows. In the example of the present disclosure shown, the fluid circulation system may include the fluid circulation, processing, and control elements between the bell nipple 128 and the swivel 120. Specifically, the fluid circulation system may include a mud pump 134 that pumps drilling fluid from a reservoir 136 through a suction line 138 into the drill string 114 at the swivel 120 through one or more fluid conduits. The fluid conduits may include pipe 140, stand-pipe 142, and hose 144. Once introduced at the swivel 120, the drilling fluid then may flow through the drill string 114, exiting at the drill bit 126 and returning through the annulus 146 between the drill string 114 and the wellbore 116 in an open-hole example, or between the drill string 114 and a casing (not shown) in a cased wellbore example. While in the wellbore 116, the drilling fluid may capture liquids and gases from the formation 108, particulates or cuttings generated by the drill bit 126 engaging with the formation, or a combination thereof.

In certain examples of the present disclosure, the fluid circulation system further may include a return line 148 coupled to the bell nipple 128. The drilling fluid may flow through the return line 148 as it exits the annulus 146 via the bell nipple 128. The fluid circulation system may also include one or more fluid treatment mechanisms coupled to the return line 148 that may separate the particulates from the returning drilling fluid before returning the drilling mud to the reservoir 136, where it can be recirculated through the drilling system 100. As depicted, the fluid treatment mechanisms may include a mud tank 150 and a shale shaker 152. The mud tank 150 may slow the flow of drilling fluid from the annulus 146 so that the drilling fluid does not flow past the shale shaker 152. The mud tank 150 may also allow for cuttings to settle and gases to be released. In certain examples of the present disclosure, the mud tank 150 may include a trap box 150*a*, which captures heavy clay particulates before the drilling fluid moves to the shale shaker 152. The shale shaker 152 may separate fine particulates from the drilling fluid using screens. The drilling fluid may flow from the fluid treatment mechanisms into the reservoir 136 through a fluid conduit 154.

The drilling system 100 may further include a fluid analyzer 158 that can receive drilling fluid samples. The fluid analyzer 158 may include a mechanism or may include integrated functionality of a larger analysis/extraction mechanism. The fluid analyzer 158 may be in fluid communication with and receive the drilling fluid samples from access points within the fluid circulation system, including but not limited to, access point **160*a* on the return line 148, access point 160*b* on the mud tank 150, access point 160*c* on the trap box 150*a*, access point 160*d* on the shale shaker 152, access point 160*e* on the suction line 138, access point 160*f* on the pipe 140, and access point 160*g* on the stand-pipe 142. The fluid communication may be provided via at least one probe at any one of the access points. In other examples, the fluid analyzer 158 may be coupled to one or more of the fluid channels such that the flow of drilling fluid passes through the fluid analyzer 158**.

Additionally, at least some of the strata **108*a-e* may contain trapped liquids and gases that are held under pressure. As the wellbore 116 penetrates new strata, some of these fluids may be released into the wellbore 116. The released fluids may become suspended or dissolved in the drilling fluid. The fluid analyzer 158 may take periodic or continuous samples of the drilling fluid, for example, by pumping, gravity drain or diversion of flow, or other suitable means. The fluid analyzer 158 may extract gas from the fluid samples to determine a chemical composition of the drilling fluid. The chemical composition may be used to determine the types of liquids and gases that are suspended or dissolved within the drilling fluid, which can then be used to determine formation characteristics of the formation 108**. In some examples, determination of the formation characteristics can be performed in real-time.

The fluid analyzer 158 may include or be communicably coupled to a computing device 165. As shown, in some examples, the computing device 165 may be located at the surface. The computing device 165 may include a processor that can execute program code stored on a machine-readable medium. For example, the computing device 165 may receive measurements associated with drilling fluid samples from the fluid analyzer 158 and may process the measurements to determine the formation characteristics. The computing device 165 may further control the operation of the fluid analyzer 158, such as by controlling how often the fluid analyzer 158 takes measurements or fluid samples.

In some examples of the present disclosure, a first drilling fluid sample can be received by the fluid analyzer 158 prior to a drilling operation. The drilling fluid sample can represent the drilling fluid that will be used during the drilling operation. The fluid analyzer 158 can position a hydrocarbon blend in contact with the first drilling fluid sample. For example, the hydrocarbon blend can be in a headspace above the first drilling fluid sample. The fluid analyzer 158 can analyze the hydrocarbon blend after the hydrocarbon blend has been in contact with the drilling fluid sample for a period of time. To do so, the fluid analyzer 158 may extract the hydrocarbon blend from the headspace and measure concentrations of components (e.g., hydrocarbon gases) of the hydrocarbon blend. The analysis of the hydrocarbon blend after the period of time can be used to determine hydrocarbon absorption by the drilling fluid. For example, the measured concentrations of the components can be compared to theoretical concentrations of the components. One or more extraction efficiency correction (EEC) factors can be determined based on the comparison. The EEC factors may then be used during subsequent analysis of drilling fluid samples by the fluid analyzer 158 to correct bias in the fluid analyzer 158.

For example, an output of the fluid analyzer 158 may include electrical signals or electrically encoded data that corresponds to measurements taken by the fluid analyzer 158 of liquids or extracted gases from a second drilling fluid sample. In certain embodiments, the computing device 165 may receive the output from the fluid analyzer 158 and determine characteristics of the liquid or extracted gas from the second drilling fluid sample, such as corresponding chemical compositions of liquid or gaseous components. The computing device 165 may, in part, determine the characteristics by correcting a bias in the measurements taken by the fluid analyzer 158 based on the one or more EEC factors.

The computing device 165 may further fully characterize a chemical composition of the second drilling fluid sample, which may have been received during the drilling operation. The chemical composition characterization of the drilling fluid sample may be based on the output from the fluid analyzer 158. Characterization of the chemical composition of the second drilling fluid sample may be more accurate due to the correction to the bias caused by fluid analyzer 158. The computing device 165 may determine the types of liquids and gases suspended within the drilling fluid sample based on the determined chemical composition. Additionally, the computing device 165 may identify fluids (e.g., oil, water, etc.) or gasses within the wellbore 116, determine formation characteristics associated with the wellbore 116, identify pay zones, or otherwise obtain information about the drilling operation using the determined types and concentrations of liquids and gases suspended within the drilling fluid.

For example, the determined chemical composition for a liquid portion of the second drilling fluid sample may be 15% chemical/compound A, 20% chemical/compound B, 60% chemical/compound C, and 5% other chemicals/compounds. Example formation characteristics may include, but are not limited to, the type of rock in the formation 108, the presences of hydrocarbons in the formation 108, the production potential for one or more of strata **108*a-e*, and the movement of fluid within one or more of strata 108*a-e*. In certain examples of the present disclosure, the computing device 165 may determine the formation characteristics using the determined chemical composition characteristics by comparing the determined chemical composition to chemical compositions of known subterranean formations. For example, the determined chemical composition may correspond to a drilling fluid with suspended fluid from a shale layer in the formation 108**.

Figure 2:
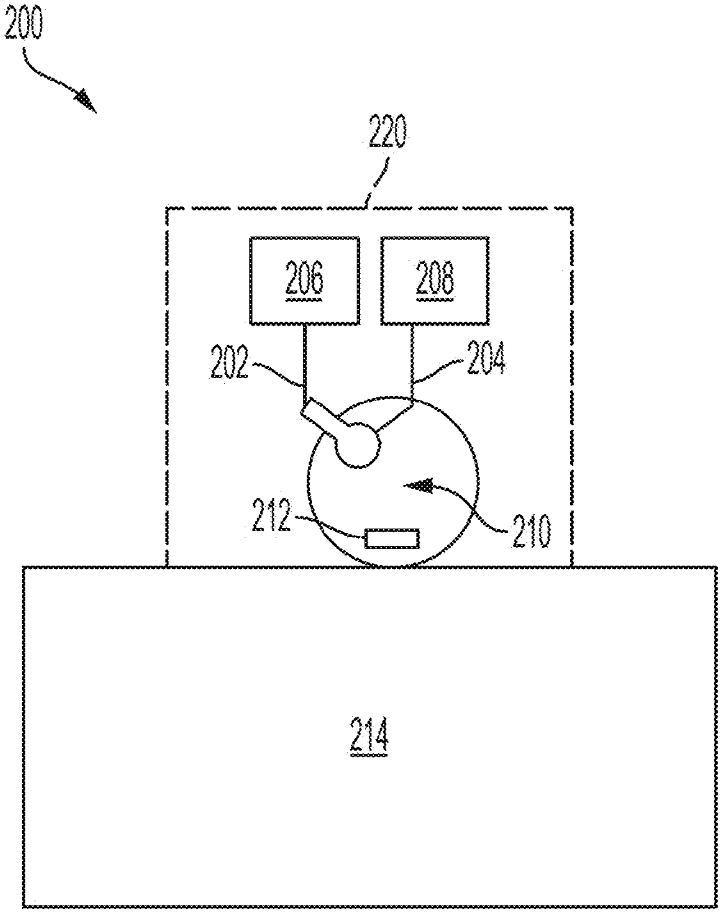
FIG. 2 is a block diagram of a system for performing small-scale extraction efficiency correction (EEC) to correct bias in gas extraction and sampling system operations, according to one example of the present disclosure.

FIG. 2 is a block diagram of a system 200 for performing small-scale extraction efficiency correction (EEC) to correct bias in gas extraction and sampling system operations, according to one example of the present disclosure. In some examples, a drilling fluid sample can be received prior to a drilling operation. The drilling fluid sample can represent a drilling fluid that will be used in the drilling operation. One or more of the components of the system 200 may be implemented by or part of a fluid analyzer 158.

In the example shown, the system 200 may receive the drilling fluid sample through a fluid conduit or pipe that leads the drilling fluid sample into a gas extractor and sampling system 220. Example gas extractor and sampling systems can include, but are not limited to, containers (e.g., flasks) with gas inlet and outlets, continuously stirred containers, distillation columns, flash columns, separator columns, bench-scale extraction vessels, constant volume/constant temperature (CVCT) gas extractors, or any other containers that allow for the separation and expansion of gas from liquids and solids. Thus, in the example, the gas extractor and sampling system 220 can include a container 210 that receives the drilling fluid sample through a fluid inlet. The container 210 can be a round-bottom flask or another suitable type of container. The gas extractor and sampling system 220 may also include a stirring mechanism 212, such as an impeller or a metal stirrer, within the container 210. In a particular example, the container 210 may be positioned on a stirring heating mantel 214 to heat the drilling fluid sample and to facilitate stirring of the drilling fluid sample by the stirring mechanism 212.

Additionally, the container 210 can be connected and in fluid communication with a calibration gas bottle 206, which can contain a hydrocarbon blend. For example, the gas extractor and sampling system 220 may include a first connection mechanism 202 through which the hydrocarbon blend may be introduced into the container 210. The first connection mechanism 202 can include a first tube, which can be connected on a first end to a gas inlet of the container 210 and can be connected on a second end to the calibration gas bottle 206. The container 210 can also be connected and in fluid communication with a gas chromatograph (GC) 208. For example, a second connection mechanism 204 can enable the GC 208 to receive and sample hydrocarbon gases of the hydrocarbon blend. The second connection mechanism 204 can include second tube, which can be connected on a first end to a gas outlet of the container 210 and can be connected on a second end to the GC 236.

In some examples, the hydrocarbon blend can be received from the calibration gas bottle 238, via the first connection mechanism 202, into a headspace of the container 210 above the drilling fluid sample. The hydrocarbon blend may be received until the GC 236 is calibrated. For example, to calibrate the GC 236, the GC 236 may sample and measure the hydrocarbon gasses of the hydrocarbon blend disposed within the headspace 204 until the GC 236 detects concentrations of the hydrocarbon gases that are similar too (e.g., within five percent) of known concentrations for the hydrocarbon gases. After calibration, the first tube and gas inlet can be disconnected from the container 210. The hydrocarbon blend may then remain in the headspace in contact with the drilling fluid sample for a period of time. After the period of time, the hydrocarbon blend can be pumped into the GC 208 for analysis.

Figure 3:
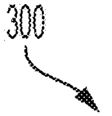
FIG. 3 is a block diagram of a system for correcting bias in gas extraction and sampling system operations using an extraction efficiency correction factor, according to one example of the present disclosure.
Figure 3:
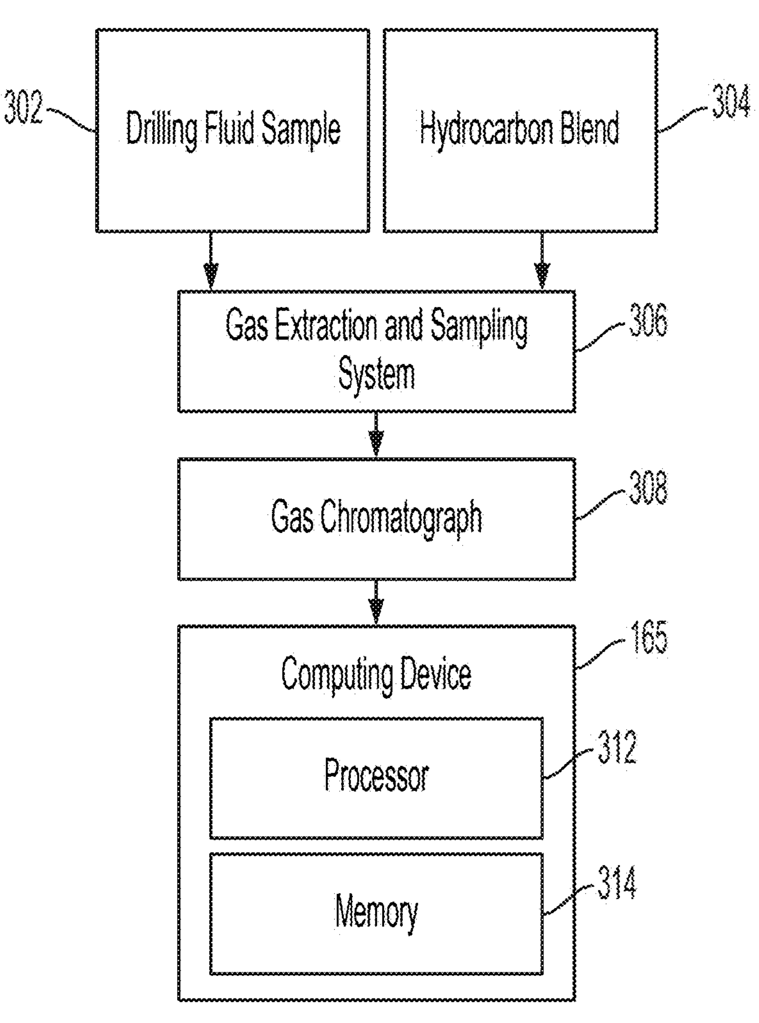

FIG. 3 is a block diagram of a system 300 for correcting bias in gas extraction and sampling system operations using an extraction efficiency correction (EEC) factor, according to one example of the present disclosure. The system 300 can include a drilling fluid sample 302, a hydrocarbon blend 304, a gas extraction and sampling system 306, a gas chromatograph (GC) 308, and a computing device 165. An example of the gas extraction and sampling system 306 is the gas extraction and sampling system 220 illustrated in FIG. 2. The drilling fluid sample 302 and the hydrocarbon blend 304 can be input into the gas extraction and sampling system 306. The hydrocarbon blend 304 can be a gaseous mixture that can include one or more hydrocarbon gases, such as methane, ethane, propane, iso-butane, n-butane, iso-pentane, n-pentane, ethylene, propylene, etc., in known volumes.

An output of the gas extraction and sampling system 306, such as an output of the hydrocarbon blend 304 from second connection mechanism 204 in FIG. 2, can be coupled to an input of the GC 308. The GC 308 can measure or otherwise determine concentrations of hydrocarbon gases in the hydrocarbon blend 304 based on the output received from the gas extraction and sampling system 306.

For example, the drilling fluid sample 302 can be stored in a container of the gas extraction and sampling system 306 for a period of time. Additionally, the hydrocarbon blend 304 can be stored in a headspace of the container and in contact with the drilling fluid sample 302 for a period of time. As a result, the drilling fluid sample 302 can at least partially absorb one or more of the hydrocarbon gases of the hydrocarbon blend 304. The hydrocarbon blend 304 can then be received via the input of the GC 308. Thus, the GC 308 can detect and measure concentrations of hydrocarbon gases in the hydrocarbon blend 304 after the hydrogen blend 304 has been in the headspace for the period of time.

Additionally, the computing device 165 can be communicatively coupled to the GC 308 to receive values for the concentrations over time of the hydrocarbon gases in the hydrocarbon blend 304. The computing device 165 can perform, by any combination of hardware, software, firmware, etc., the operations described herein. For example, the computing device 165 can include a processor 312 that executes program code stored in a memory 314 also included in the computing device 165. As further described below, the computing device 165 may plot the concentration over time for each of the hydrocarbon gases based on the values from the GC 308. In doing so, the computing device 165 can generate a decay curve for each of the hydrocarbon gases. The computing device 165 can also determine, based on the decay curves, volumes for each hydrocarbon gases. The computing device 165 may then compare the determined volumes to the known volumes for each of the hydrocarbon gases to determine an EEC factor for each of the hydrocarbon gases.

The computing device 165 can further correct bias caused by the gas extraction and sampling system 306 during subsequent gas extraction and sampling system operations using the EEC factors. For example, the gas extraction and sampling system 306 may extract gas from a second drilling fluid sample during a wellbore operation and may analyze the gas via the GC 308. The computing device 165 may receive data from the extraction and analysis of the second drilling fluid sample and may correct bias in the data based on the EEC factors.

Figure 4:
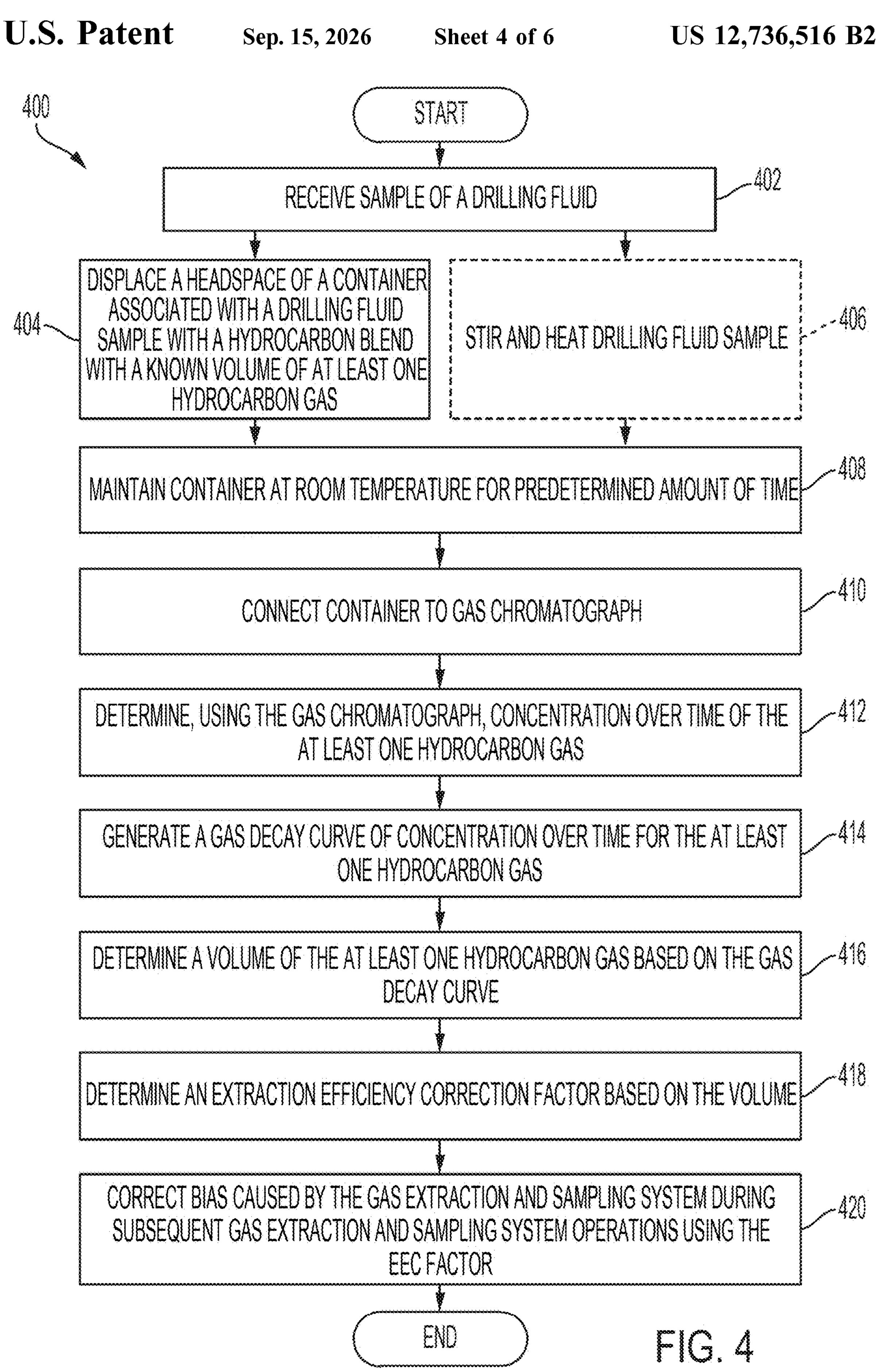
FIG. 4 is a flowchart of a process for correcting bias in gas extraction and sampling system operations using an extraction efficiency correction factor, according to one example of the present disclosure.

FIG. 4 is a flowchart of a process for correcting bias in gas extraction and sampling system operations using an extraction efficiency correction (EEC) factor, according to one example of the present disclosure. The process 400 may be performed by software, firmware, hardware or a combination thereof. At block 402, the process 400 involves receiving a drilling fluid sample at a container. The drilling fluid sample can be relatively small (e.g. contained in a bench-scale flask or other suitable container). For example, the drilling fluid sample may be a two hundred and fifty milliliter sample. The drilling fluid sample can represent a drilling fluid that is or will be used during a drilling operation such as depicted and described with respect to the drilling system 100 of FIG. 1.

At block 404, the process 400 involves displacing a headspace of the container associated with a drilling fluid sample with a hydrocarbon blend with a known volume of at least one hydrocarbon gas. In some examples, the headspace can be displaced by connecting a container of a gas extraction and sampling system with a calibration gas bottle. For example, a tube may be connected to the calibration gas bottle on a first end and to a gas inlet of the container on a second end. Then, the hydrogen blend can be transferred from the calibration gas bottle to the headspace of the container via the tube. The hydrocarbon gases of the hydrocarbon blend can include methane, ethane, propane, isobutane, n-butane, iso-pentane, n-pentane, ethylene, propylene, or any suitable combination of the foregoing.

At block 406, the process 400 involves stirring and heating the drilling fluid sample. The stirring and heating may occur at the same time as the displacing of the headspace associated with the drilling fluid sample with the hydrocarbon blend at block 404. In an example, the container may be placed on a stirring heating mantle and a magnetic stirrer can be placed in drilling fluid sample in the container. Thus, the stirring heating mantle can heat the drilling fluid sample and can facilitate the stirring of the drilling fluid sample by the magnetic stirrer. In some examples, stirring the drilling fluid sample, heating the drilling fluid sample, or a combination thereof at block 406 may be optional.

At block 408, the process 400 involves maintaining the container at room temperature for a predetermined amount of time. In some examples of the present disclosure, the predetermined amount of time is at least thirty minutes. In additional examples, the predetermined amount of time can be at least two hours. During the predetermined amount of time, the drilling fluid sample may at least partially absorb one or more of the hydrocarbon gases of the hydrocarbon blend.

At block 410, the process 400 involves connecting the container to a gas chromatograph (GC) or similar type of equipment. In some examples, the container can be connected to the GC prior to receiving the drilling fluid sample. Additionally, in an example, a tube or pump may connect a gas outlet of the container to the GC.

At block 412, the process 400 involve determining, using the GC, concentration over time of the at least one hydrocarbon gas. For example, after connection of the container to the GC, the hydrocarbon blend in the headspace can be pumped into the GC at a known flow rate. The GC can then perform a gas concentration measurement and other analyses on the hydrocarbon blend. For example, the GC can determine the concentration over time for each of the hydrocarbon gases of the hydrogen blend received from the headspace of the container. The GC may perform the gas concentration measurement and other analyses until the concentration over time of the at least one hydrocarbon gases is less than a predetermined threshold (e.g., a gas chromatography limit of quantification (LOQ)).

Figure 5:
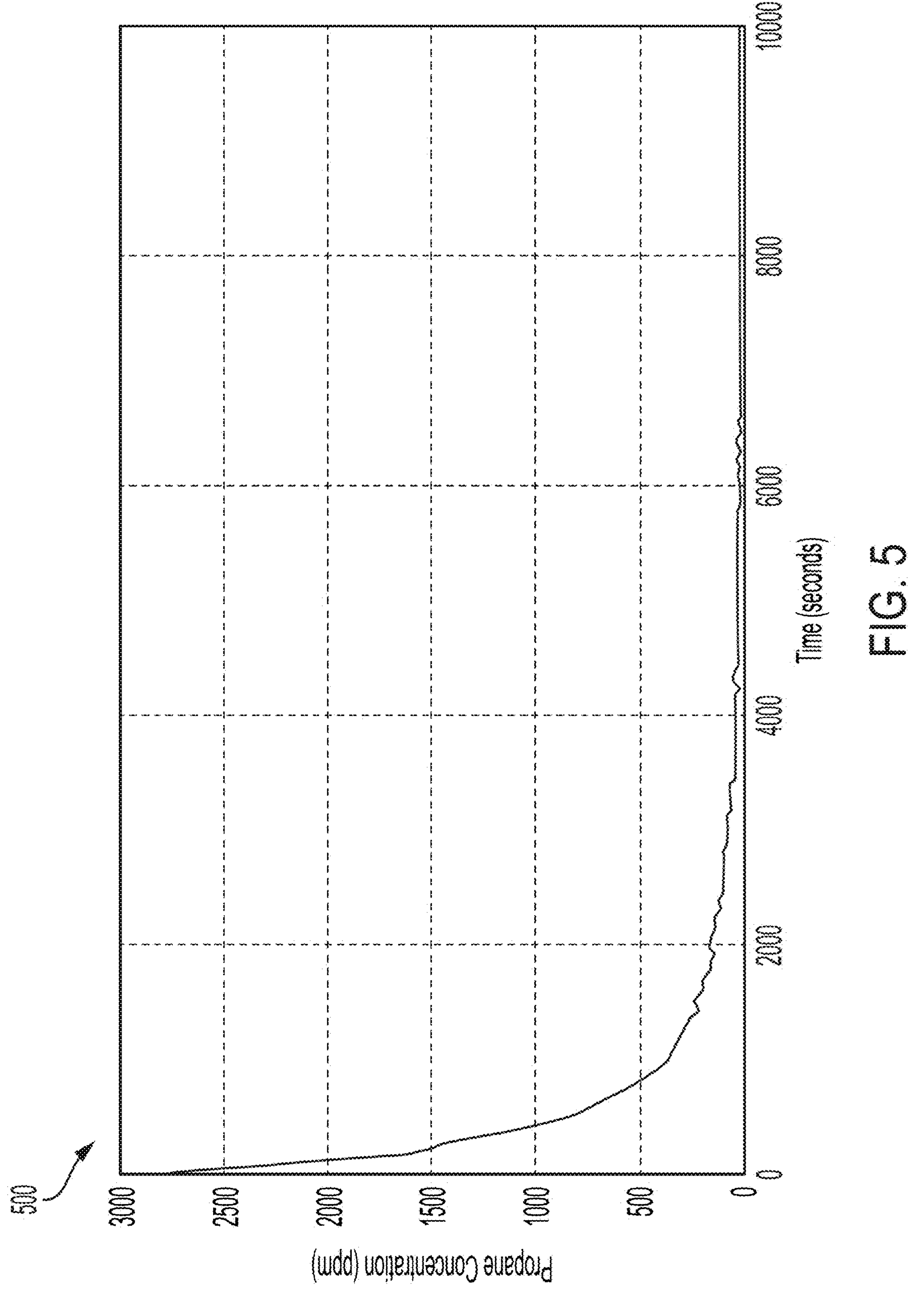
FIG. 5 depicts an example of a gas decay curve, according to one example of the present disclosure.

At block 414, the process 400 involves generating a decay curve of concentration over time for the at least one hydrocarbon gas. Thus, the decay curve can represent concentration of each hydrocarbon gas detected in the hydrocarbon blend extracted from the headspace versus time. For example, with reference to FIG. 3, the computing device 165 may receive the concentration of each hydrocarbon gas from the GC 308 and plot a concentration of each hydrocarbon gas versus time. To illustrate, FIG. 5 depicts a gas decay curve 500 of propane concentration in parts per million (PPM) along the Y-axis and time in seconds along the X-axis.

At block 416, the process 400 involves determining a volume of the at least one hydrocarbon gas based on the gas decay curve. For example, the volume can be determined by calculating an area under the gas decay curve for each of the hydrocarbon gases. Additionally, in some examples, the known flow rate for the pump can be used to determine the volume of each of the hydrocarbon gases.

At block 418, the process 400 involves determining an extraction efficiency correction (EEC) factor based on the volume of the at least one hydrocarbon gas. For example, the EEC factor for a hydrocarbon gas can be determined by dividing the known concentration of the hydrocarbon gas for the hydrocarbon blend with the volume determined based on the gas decay curve for the hydrocarbon gas.

As an example of determining the EEC factor, Table 1 illustrates testing results of small-scale EEC of water-based mud (WBM). In Table, 2 the hydrocarbon blend is comprised on methane, ethane, propane, isobutane (i-butane), normal butane (n-butane), isopentane (i-pentane), and normal pentane (n-pentane). Additionally, in Table 2, the average total volume from the headspace of the container is provided for each hydrocarbon gas of the hydrocarbon blend in standard cubic centimeters per minute (sccm). The average total volume from the headspace can be the volume determined based on the concentration over time for each hydrocarbon gas as provided by the GC. The theoretical total volumes of each hydrocarbon gas can be divided by the average total volumes from the headspace to provide EEC factors for each hydrocarbon gas. The differences between the average total volumes and the theoretical total volumes can indicate that at least a portion of each hydrocarbon was absorbed by the WBM over time.

TABLE 1

| | Methane | Ethane | Propane | i-Butane | n-Butane | i-Pentane | n-Pentane |
|---|---|---|---|---|---|---|---|
| Average Total Volume from Headspace (sccm) | 23.149 | 5.783 | 2.368 | 0.951 | 0.698 | 0.338 | 0.331 |
| Theoretical Total Volume (sccm) | 25 | 6.25 | 2.5 | 1 | 0.75 | 0.375 | 0.375 |
| EEC Factor | 1.080 | 1.081 | 1.056 | 1.051 | 1.074 | 1.110 | 1.132 |

At block 420, the process 400 involves correcting bias caused by the gas extraction and sampling system during subsequent gas extraction and sampling system operations using the EEC factors. For example, the gas extraction and sampling system may extract gas from a second drilling fluid sample during a wellbore operation and may analyze the gas via the GC. Then, bias in data from the extraction and analysis of the second drilling fluid sample can be corrected by applying an EEC factor for a hydrocarbon gas to data for the hydrocarbon gas. Thus, in some examples, the process 400 can involve correcting bias, in real-time, in wellbore data obtained during a wellbore operation using the EEC factors.

FIG. 5 depicts an example of a gas decay curve 500, according to one example of the present disclosure. In particular, FIG. 5 depicts an example of the gas decay curve 500 for propane. In some examples of the present disclosure, a total concentration per time value can be generated by integrating an area under the gas decay curve 500, which can be a concentration over time curve, at each of a series of points in time. In this manner, the integration can generate area under the curve data by calculating an area under the curve for each time point. Results of the integration can be used to determine a total volume for propane. Then, the total volume may be compared to a theoretical volume to determine an extraction efficiency correction factor.

Figure 6:
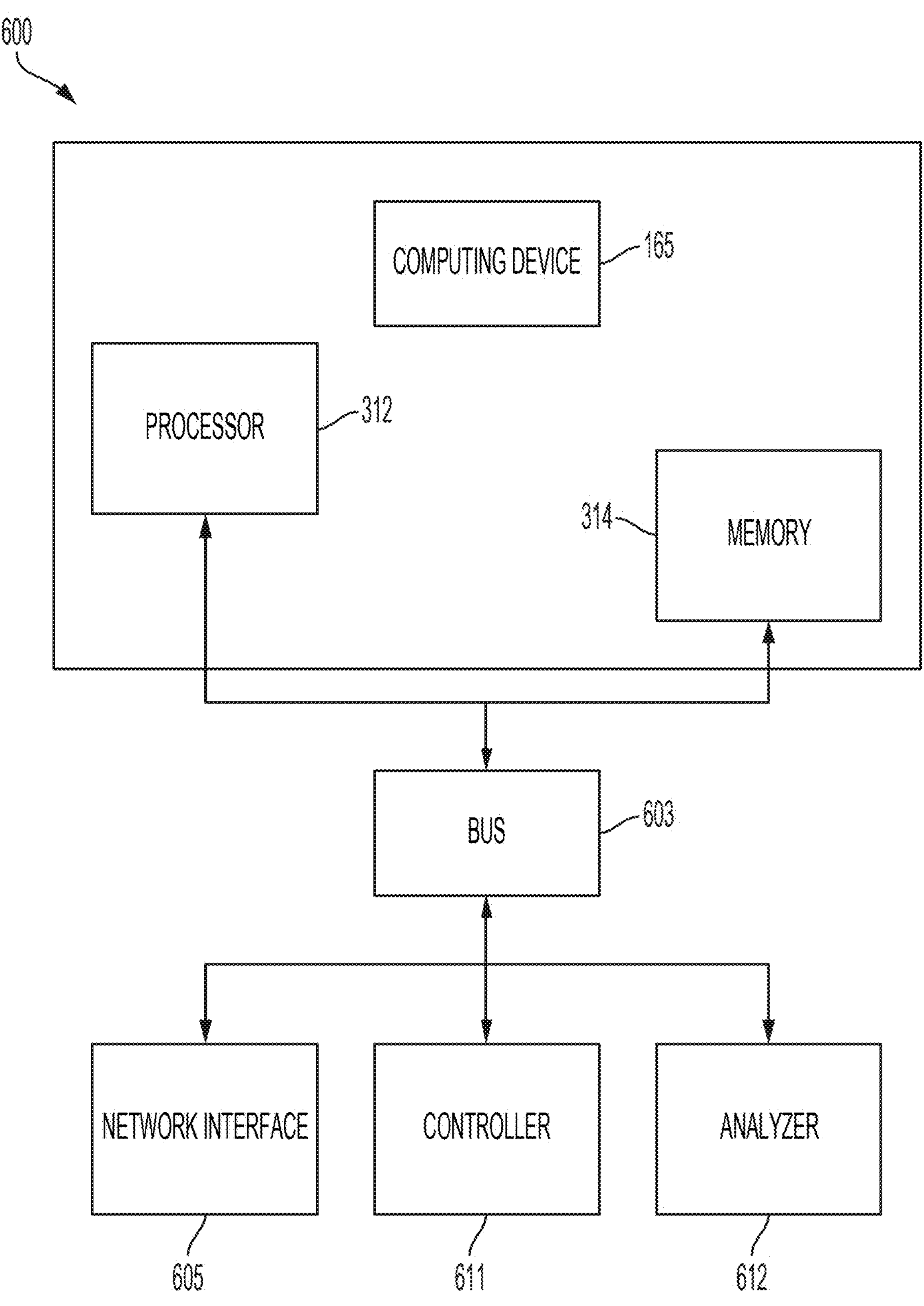
FIG. 6 is a block diagram of a computing environment, according to one example of the present disclosure.

FIG. 6 is a block diagram of a computing environment, according to one example of the present disclosure. The computer includes a processor 312 (possibly including multiple processors, multiple cores, multiple nodes, or implementing multi-threading, etc.) The computer includes a memory 314. The memory 314 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 603 (e.g., PCI, ISA, PCI-Express, Hyper-Transport® bus, InfiniBand® bus, NuBus, etc.) and a network interface 1205 (e.g., a Fiber Channel interface, an Ethernet interface, an internet small computer system interface, SONET interface, wireless interface, etc.).

The computer also includes an analyzer 612 and a controller 611. The analyzer 612 can perform processing and analyzing of a drilling fluid sample (as described above). The controller 611 can control the different operations that can occur in the response to results from the analysis. For example, the controller 611 can communicate instructions to the appropriate equipment, devices, etc. to alter different hydrocarbon recovery operations. Any one of the previously described functionalities may be partially (or entirely) implemented in hardware or on the processor 312. For example, the functionality may be implemented with an application specific integrated circuit, in logic implemented in the processor 312, in a co-processor on a peripheral or card, etc. Further, realizations may include fewer or additional components not illustrated in FIG. 6 (e.g., video cards, audio cards, additional network interfaces, peripheral devices etc.). The processor 312 and the network interface 605 are coupled to the bus 603. Although illustrated as being coupled to the bus 603, the memory 314 may be coupled to the processor 312.

As will be appreciated, aspects of the present disclosure may be depicted as a system, method or program code/instructions stored in one or more machine-readable media. Accordingly, aspects may take the form of hardware, software (including firmware, resident software, micro-code, etc.), or a combination of software and hardware aspects that may generally be referred to herein as a "circuit", "module" or "system". The functionality presented as individual modules/units in the example illustrations can be organized differently in accordance with any one of platform (operating system or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain or store a program for use by or in connection with an instruction execution system, apparatus, or device. A machine-readable storage medium is not a machine-readable signal medium.

A machine-readable signal medium may include propagated data signal with machine-readable program code depicted therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code depicted on a machine-readable medium may be transmitted using an appropriate medium, including but not limited to wireless, wireline, optical fiber cable, RF, etc., or any suitable combination of the foregoing. Computer program code for carrying out operations for aspects of the disclosure may be written in any combination of one or more programming languages, including an object oriented programming language such as Java® programming language, C++ or the like; a dynamic programming language such as Python; a scripting language such as Perl programming language or PowerShell script language; and conventional procedural programming languages, such as the "C" programming language or similar programming languages. The program code may execute in a distributed manner across multiple machines and may execute on one machine while providing results or accepting input on another machine.

Using the apparatus, systems, and methods disclosed herein may provide the ability to monitor changes in wellbore particles (e.g., cuttings), so that the impact of drilling fluid properties and activities in the field can be assessed immediately. This ability may be used to increase efficiency by redirecting pumping and drilling operations in real-time, perhaps as part of a closed-loop control system. While the aspects of the disclosure are described with reference to various implementations and exploitations, it will be understood that these aspects are illustrative and that the scope of the claims is not limited to them. In general, techniques for processing and analyzing of particles from wellbore operations as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary. Particular operations are illustrated in the context of specific illustrative examples. Other allocations of functionality are envisioned and may fall within the scope of the disclosure. Use of the phrase "at least one of" preceding a list with the conjunction "and" should not be construed as a list of categories with one item from each category, unless specifically stated otherwise. A clause that recites "at least one of A, B, and C" can be infringed with only one of the listed items, multiple of the listed items, and one or more of the items in the list and another item not listed.

In some aspects, systems and methods for predicting bias caused by partial absorption of a hydrocarbon blend by a drilling fluid sample during wellbore operations are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a method comprising: controlling a gas extraction and sampling system to displace a headspace of a container associated with a drilling fluid sample with a hydrocarbon blend comprising a first volume of at least one hydrocarbon gas; controlling the gas extraction and sampling system to extract the hydrocarbon blend from the headspace associated with the drilling fluid sample; determining a concentration over time of the at least one hydrocarbon gas of the hydrocarbon blend; generating a gas decay curve of the concentration over time of the at least one hydrocarbon gas of the hydrocarbon blend; determining, based on the gas decay curve, a second volume of the at least one hydrocarbon gas; determining an extraction efficiency correction factor based on a ratio of the first volume to the second volume; and correcting bias caused by the gas extraction and sampling system during subsequent gas extraction and system operations using the extraction efficiency correction factor.

Example 2 is the method of example(s) 1, further comprising correcting bias, in real-time, in wellbore data obtained during a wellbore operation using the extraction efficiency correction factor to identify fluids or gasses in a wellbore associated with the wellbore operation or to identify formation characteristics associated with the wellbore.

Example 3 is the method of example(s) 1-2, further comprising determining, based on the gas decay curve, the second volume of the at least one hydrocarbon gas by calculating an area under the gas decay curve for the at least one hydrocarbon gas.

Example 4 is the method of example(s) 1-3, further comprising stirring the drilling fluid sample while displacing the headspace associated with the drilling fluid sample with the hydrocarbon blend.

Example 5 is the method of example(s) 1-4, further comprising controlling the gas extraction and sampling system to cause the drilling fluid sample to at least partially absorb the at least one hydrocarbon gas of the hydrocarbon blend.

Example 6 is the method of example(s) 1-5, further comprising determining the concentration over time of the at least one hydrocarbon gas of the hydrocarbon blend by analyzing the hydrocarbon blend using gas chromatography until the concentration over time of the at least one hydrocarbon gas is less than a predetermined threshold.

Example 7 is the method of example(s) 1-6, further comprising prior to generating the gas decay curve, heating the drilling fluid sample to a predetermined temperature.

Example 8 is the method of example(s) 1-7, further comprising calibrating a gas chromatograph using a calibration gas bottle, wherein the calibration gas bottle is connectable to the container.

Example 9 is a system comprising: a gas extraction and sampling system positionable to: displace a headspace of a container associated with a drilling fluid sample with a hydrocarbon blend with a first volume of at least one hydrocarbon gas; and extract the hydrocarbon blend from the headspace associated with the drilling fluid sample; a gas chromatograph connectable to the gas extraction and sampling system to determine a concentration over time of at least one hydrocarbon gas of the hydrocarbon blend; a processor; and a memory that includes instructions executable by the processor for causing the processor to: generate a gas decay curve of the concentration over time of the at least one hydrocarbon gas of the hydrocarbon blend; determine, based on the gas decay curve, a second volume of the at least one hydrocarbon gas; determine an extraction efficiency correction factor based on a ratio of the first volume to the second volume; and correct bias caused by the gas extraction and sampling system during subsequent gas extraction and system operations using the extraction efficiency correction factor.

Example 10 is the system of example(s) 9, wherein the gas extraction and sampling system comprises a calibration gas bottle, wherein the container is a round-bottom flask, and wherein the round-bottom flask is connectable to the calibration gas bottle.

Example 11 is the system of example(s) 9-10, wherein the memory further comprises instructions executable by the processor for causing the processor to correct bias, in real-time, in wellbore data obtained during a wellbore operation using the extraction efficiency correction factor to identify fluids or gasses in a wellbore associated with the wellbore operation or to identify formation characteristics associated with the wellbore.

Example 12 is the system of example(s) 9-11, wherein the memory further comprises instructions executable by the processor for causing the processor to determine, based on the gas decay curve, the second volume of the at least one hydrocarbon gas by calculating an area under the gas decay curve for the at least one hydrocarbon gas.

Example 13 is the system of example(s) 9-12, wherein the gas extraction and sampling system is further positionable to stir the drilling fluid sample while displacing the headspace associated with the drilling fluid sample with the hydrocarbon blend.

Example 14 is the system of example(s) 9-13, wherein the gas extraction and sampling system is further positionable to cause the drilling fluid sample to at least partially absorb the at least one hydrocarbon gas of the hydrocarbon blend.

Example 15 is the system of example(s) 9-14, wherein the gas chromatograph is further connectable to the gas extraction and sampling system to determine the concentration over time of at least one hydrocarbon gas of the hydrocarbon blend by analyzing the hydrocarbon blend until the concentration over time of the at least one hydrocarbon gas is less than a predetermined threshold.

Example 16 is the system of example(s) 9-15, wherein the gas extraction and sampling system is further positionable to heat the drilling fluid sample to a predetermined temperature.

Example 17 is a non-transitory computer-readable medium comprising instructions that are executable by a processor for causing the processor to perform operations comprising: determining a concentration over time of at least one hydrocarbon gas of a hydrocarbon blend with a first volume of the at least one hydrocarbon gas, wherein the hydrocarbon blend displaces a headspace of a container associated with a drilling fluid sample in a gas extraction and sampling system; generating a gas decay curve of the concentration over time of the at least one hydrocarbon gas of the hydrocarbon blend; determining, based on the gas decay curve, a second volume of the at least one hydrocarbon gas; determining an extraction efficiency correction factor based on a ratio of the first volume to the second volume; and correcting bias caused by the gas extraction and sampling system during subsequent gas extraction and system operations using the extraction efficiency correction factor.

Example 18 is the non-transitory computer-readable medium of example(s) 17, further comprising instructions that are executable by the processor for causing the processor to perform operations comprising correcting bias, in real-time, in wellbore data obtained during a wellbore operation using the extraction efficiency correction factor to identify fluids or gasses in a wellbore associated with the wellbore operation or to identify formation characteristics associated with the wellbore.

Example 19 is the non-transitory computer-readable medium of example(s) 17-18, further comprising instructions that are executable by the processor for causing the processor to perform operations comprising determining, based on the gas decay curve, the second volume of the at least one hydrocarbon gas by calculating an area under the gas decay curve for the at least one hydrocarbon gas.

Example 20 is the non-transitory computer-readable medium of example(s) 17-19, further comprising instructions that are executable by the processor for causing the processor to perform operations comprising determining the concentration over time of the at least one hydrocarbon gas of the hydrocarbon blend by analyzing the hydrocarbon blend using gas chromatography until the concentration over time of the at least one hydrocarbon gas is less than a predetermined threshold.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:

controlling a gas extraction and sampling system to displace a headspace of a container associated with a drilling fluid sample with a hydrocarbon blend comprising a first volume of at least one hydrocarbon gas;

controlling the gas extraction and sampling system to extract the hydrocarbon blend from the headspace associated with the drilling fluid sample;

determining a concentration over time of the at least one hydrocarbon gas of the hydrocarbon blend;

generating a gas decay curve of the concentration over time of the at least one hydrocarbon gas of the hydrocarbon blend;

determining, based on the gas decay curve, a second volume of the at least one hydrocarbon gas;

determining an extraction efficiency correction factor based on a ratio of the first volume to the second volume; and correcting bias caused by the gas extraction and sampling system during subsequent gas extraction and system operations using the extraction efficiency correction factor.

2. The method of claim 1, further comprising correcting bias, in real-time, in wellbore data obtained during a wellbore operation using the extraction efficiency correction factor to identify fluids or gasses in a wellbore associated with the wellbore operation or to identify formation characteristics associated with the wellbore.

3. The method of claim 1, further comprising determining, based on the gas decay curve, the second volume of the at least one hydrocarbon gas by calculating an area under the gas decay curve for the at least one hydrocarbon gas.

4. The method of claim 1, further comprising stirring the drilling fluid sample while displacing the headspace associated with the drilling fluid sample with the hydrocarbon blend.

5. The method of claim 1, further comprising controlling the gas extraction and sampling system to cause the drilling fluid sample to at least partially absorb the at least one hydrocarbon gas of the hydrocarbon blend.

6. The method of claim 1, further comprising determining the concentration over time of the at least one hydrocarbon gas of the hydrocarbon blend by analyzing the hydrocarbon blend using gas chromatography until the concentration over time of the at least one hydrocarbon gas is less than a predetermined threshold.

7. The method of claim 1, further comprising prior to generating the gas decay curve, heating the drilling fluid sample to a predetermined temperature.

8. The method of claim 7, further comprising calibrating a gas chromatograph using a calibration gas bottle, wherein the calibration gas bottle is connectable to the container.

9. A system comprising:

a gas extraction and sampling system positionable to:

displace a headspace of a container associated with a drilling fluid sample with a hydrocarbon blend with a first volume of at least one hydrocarbon gas; and extract the hydrocarbon blend from the headspace associated with the drilling fluid sample;

a gas chromatograph connectable to the gas extraction and sampling system to determine a concentration over time of at least one hydrocarbon gas of the hydrocarbon blend;

a processor; and a memory that includes instructions executable by the processor for causing the processor to:

generate a gas decay curve of the concentration over time of the at least one hydrocarbon gas of the hydrocarbon blend;

determine, based on the gas decay curve, a second volume of the at least one hydrocarbon gas;

determine an extraction efficiency correction factor based on a ratio of the first volume to the second volume; and correct bias caused by the gas extraction and sampling system during subsequent gas extraction and system operations using the extraction efficiency correction factor.

10. The system of claim 9, wherein the gas extraction and sampling system comprises a calibration gas bottle, wherein the container is a round-bottom flask, and wherein the round-bottom flask is connectable to the calibration gas bottle.

11. The system of claim 9, wherein the memory further comprises instructions executable by the processor for causing the processor to correct bias, in real-time, in wellbore data obtained during a wellbore operation using the extraction efficiency correction factor to identify fluids or gasses in a wellbore associated with the wellbore operation or to identify formation characteristics associated with the wellbore.

12. The system of claim 9, wherein the memory further comprises instructions executable by the processor for causing the processor to determine, based on the gas decay curve, the second volume of the at least one hydrocarbon gas by calculating an area under the gas decay curve for the at least one hydrocarbon gas.

13. The system of claim 9, wherein the gas extraction and sampling system is further positionable to stir the drilling fluid sample while displacing the headspace associated with the drilling fluid sample with the hydrocarbon blend.

14. The system of claim 9, wherein the gas extraction and sampling system is further positionable to cause the drilling fluid sample to at least partially absorb the at least one hydrocarbon gas of the hydrocarbon blend.

15. The system of claim 9, wherein the gas chromatograph is further connectable to the gas extraction and sampling system to determine the concentration over time of at least one hydrocarbon gas of the hydrocarbon blend by analyzing the hydrocarbon blend until the concentration over time of the at least one hydrocarbon gas is less than a predetermined threshold.

16. The system of claim 9, wherein the gas extraction and sampling system is further positionable to heat the drilling fluid sample to a predetermined temperature.

17. A non-transitory computer-readable medium comprising instructions that are executable by a processor for causing the processor to perform operations comprising:

determining a concentration over time of at least one hydrocarbon gas of a hydrocarbon blend with a first volume of the at least one hydrocarbon gas, wherein the hydrocarbon blend displaces a headspace of a container associated with a drilling fluid sample in a gas extraction and sampling system;

generating a gas decay curve of the concentration over time of the at least one hydrocarbon gas of the hydrocarbon blend;

determining, based on the gas decay curve, a second volume of the at least one hydrocarbon gas;

determining an extraction efficiency correction factor based on a ratio of the first volume to the second volume; and correcting bias caused by the gas extraction and sampling system during subsequent gas extraction and system operations using the extraction efficiency correction factor.

18. The non-transitory computer-readable medium of claim 17, further comprising instructions that are executable by the processor for causing the processor to perform operations comprising correcting bias, in real-time, in wellbore data obtained during a wellbore operation using the extraction efficiency correction factor to identify fluids or gasses in a wellbore associated with the wellbore operation or to identify formation characteristics associated with the wellbore.

19. The non-transitory computer-readable medium of claim 17, further comprising instructions that are executable by the processor for causing the processor to perform operations comprising determining, based on the gas decay curve, the second volume of the at least one hydrocarbon gas by calculating an area under the gas decay curve for the at least one hydrocarbon gas.

20. The non-transitory computer-readable medium of claim 17, further comprising instructions that are executable by the processor for causing the processor to perform operations comprising determining the concentration over time of the at least one hydrocarbon gas of the hydrocarbon blend by analyzing the hydrocarbon blend using gas chromatography until the concentration over time of the at least one hydrocarbon gas is less than a predetermined threshold.

* * * * *